United States Patent
Ujita

(10) Patent No.: US 7,164,047 B2
(45) Date of Patent: Jan. 16, 2007

(54) PROCESSES FOR PREPARATION OF CYCLOPROPYLETHANOL, CYCLOPROPYLACETONITORILE AND INTERMEDIATES OF BOTH

(75) Inventor: Katsuji Ujita, Niigata (JP)

(73) Assignee: Kuraray Co., Ltd., Kurashiki (JP)

( * ) Notice: Subject to any disclaimer, the term of this patent is extended or adjusted under 35 U.S.C. 154(b) by 476 days.

(21) Appl. No.: 10/493,224

(22) PCT Filed: Oct. 31, 2002

(86) PCT No.: PCT/JP02/11345

§ 371 (c)(1),
(2), (4) Date: May 6, 2004

(87) PCT Pub. No.: WO03/042145

PCT Pub. Date: May 22, 2003

(65) Prior Publication Data

US 2005/0020846 A1 Jan. 27, 2005

(30) Foreign Application Priority Data

Nov. 12, 2001 (JP) ............................. 2001-345555
Feb. 6, 2002 (JP) ............................. 2002-029169

(51) Int. Cl.
*C07C 29/14* (2006.01)
*C07C 253/30* (2006.01)
*C07C 249/08* (2006.01)
*C07C 255/31* (2006.01)

(52) U.S. Cl. ............ 568/700; 568/420; 558/308; 558/311; 558/313; 558/434; 564/253; 564/259

(58) Field of Classification Search ............... 568/700, 568/420; 558/434, 308, 311, 313; 564/253, 564/259
See application file for complete search history.

(56) References Cited

U.S. PATENT DOCUMENTS 1,899,340 A 2/1933 Knorr et al.
3,876,682 A 4/1975 Henrick et al.

FOREIGN PATENT DOCUMENTS

| EP | 285890 | 10/1988 |
|---|---|---|
| JP | 63-233976 | 9/1988 |
| JP | WO 97/03949 | 2/1997 |
| JP | 11-510487 | 9/1999 |
| WO | WO 00/63163 | 10/2000 |

OTHER PUBLICATIONS

Hiroaki Ueno, et al., "Synthesis and Evaluation of Antiinflammatory Activities of a Series of Corticosteroid 17 α-Esters Containing a Functional Group", J. Med. Chem., vol. 34, No. 8, 1991, pp. 2468-2477.

Qun Li, et al, "Synthesis and Structure-Activity Relationships of 2-Pyridones: A Novel Series of Potent DNA Gyrase Inhibitors as Antibacterial Agents", J. Med. Chem., vol. 39, No. 16, 1996, pp. 3070-3088.

John M. Janusz, et al., "New Cyclooxygenase-2/5-Lipoxygenase Inhibitors. 3.7-tert-Butyl-2-3-dihydro-3,3-dimethylbenzofuran Derivatives as Gastrointestinal Safe Antiinflammatory and Analgesic Agents: Variations at the 5 Position", J. Med. Chem., vol. 41, No. 18, 1998, pp. 3515-3529.

Ioannis M. Takakis, et al., "Cyclopropanation of Some Simple Olefinic Compounds. Byproduct Formation in Excess Simmons-Smith Reagent", J. Org. Chem., vol. 43, No. 18, 1978, pp. 3496-3500.

Shinya Nishida, et al., "Directive Effect of the Cyclopropyl Group in Hydroboration", J. Org. Chem., vol. 32, Apr. 1967, pp. 939-942.

Harold Hart, et al., "The Effect of Ring Size on Diacyl Peroxide Decompositions", J. Am. Chem. Soc., vol. 81, Sep. 20, 1959, pp. 4891-4896.

R. H. Mizzoni, et al., "Anticoccidial Activity in 1-[2-(Cycloalkyl)- and 2-(Cycloalkylmethyle 1-4-amino-5-pyrimidyl)methyl]pyridinium Salts", Journal of Medicinal Chemistry, vol. 13, No. 5, 1970, pp. 878-882.

George E. Cartier, et al., "The Reaction of 2-Cyclopropylethylamine-1-$^{14}$C with Nitrous Acid", J. Am. Chem. Soc., vol. 85, Apr. 1963, pp. 932-937.

*Primary Examiner*—Elvis O. Price
(74) *Attorney, Agent, or Firm*—Oblon, Spivak, McClelland, Maier & Neustadt, P.C.

(57) ABSTRACT

A process for preparation of cyclopropylethanol, which comprises subjecting a 3-cyclopropyl-2,3-epoxypropionic acid ester to solvolysis, treating the product of the solvolysis with an acid to obtain cyclopropylacetaldehyde, and reducing the obtained cyclopropylacetaldehyde; and a process for preparation of cyclopropylacetonitrile, which comprises subjecting a 3-cyclopropyl-2,3-epoxypropionic acid ester to solvolysis in the presence of a base, treating the product of the solvolysis with an acid to obtain cyclopropylacetaldehyde, reacting the obtained cyclopropylacetaldehyde with hydroxylamine or salts thereof to obtain cyclopropaneacetaldehyde oxime, and reacting the obtained cyclopropaneacetaldehyde oxime with acetic anhydride. According to the present invention, cyclopropylethanol and cyclopropylacetonitrile can be prepared at low costs and industrially advantageously.

15 Claims, No Drawings

PROCESSES FOR PREPARATION OF CYCLOPROPYLETHANOL, CYCLOPROPYLACETONITORILE AND INTERMEDIATES OF BOTH

TECHNICAL FIELD

The present invention relates to processes for preparation of cyclopropylethanol, cyclopropylacetonitrile and intermediates of both. The cyclopropylethanol obtained by the process of the present invention is useful as an intermediate for synthesizing pharmaceutical and agricultural chemicals, and cyclopropylacetonitrile obtained by the process of the present invention is useful as an intermediate for synthesizing various pharmaceuticals [see, for example, J. Med. Chem. 34, 2468(1991); J. Med. Chem. 39, 3070(1996) and J. Med. Chem. 41, 3515(1998)].

BACKGROUND ART

Known processes for preparation of cyclopropylethanol are, for example, (1) a process which comprises reacting homoallyl alcohol with diazomethane [J. Org. Synth. 43, 3496(1978)], (2) a process which comprises reacting butadiene with dibromocarbene to obtain 1,1-dibromo-2-vinyl-cyclopropane, debrominating the obtained product with metallic sodium-alcohol to synthesize vinylcyclopropane and subjecting the vinylcylopropane to hydroboronation-oxidation [J. Org. Synth. 32, 939(1967)], and (3) a process which comprises reacting lithium cyclopropylate and ethylene oxide [J. Am. Chem. Soc. 81, 4891(1959)].

The above process (1) uses an explosive diazomethane. The above process (2) has to use, to form dibromocarbene, bromoform, which is carcinogenic and also uses metallic sodium, which is explosive. The above process (3) uses a toxic gas of ethylene oxide. These processes are therefore all not industrially advantageous processes for preparation of cyclopropylethanol.

Known processes for preparation of cyclopropylacetonitrile are, for example, (4) a process which comprises reacting cyclopropylmethyl bromide in the presence of a phase transfer catalyst with an alkali metal cyanide in a solvent of water [WO00/63163], (5) a process which comprises reacting cyclopropylmethyl bromide with an alkali metal cyanide in dimethyl sulfoxide [J. Med. Chem. 13, 878(1970)], and (6) a process which comprises reacting cyclopropylmethyl bromide with an alkali metal cyanide in a solvent of ethanol [J. Am. Chem. Soc., 85, 932(1963)]. A process (7) is known for preparation of cyclopropanecarbonitrile, which comprises dehydrating cyclopropanecarbaldehyde oxime with formic acid [Tokuhyo-Hei 11-510487].

The above processes (4), (5) and (6), all using a toxic alkali metal cyanide, are not industrially advantageous processes for preparation of cyclopropylacetonitrile. The above process (7), which comprises neutralizing the reaction mixture obtained by the dehydration with an alkali metal compound, requires treatment of the effluent containing a large amount of the alkali metal formate byproduced on the neutralization. This process, when applied to preparation of cyclopropylacetonitrile, does not provide an industrially advantageous process.

Accordingly, an object of the present invention is to provide a process for preparing cyclopropylethanol at a low cost and industrially advantageously.

Another object of the present invention is to provide a process for preparing cyclopropylacetonitrile industrially advantageously.

Still another object of the present invention is to provide processes for preparing, industrially advantageously, intermediates for synthesizing cyclopropylethanol and cyclopropylacetonitrile.

DISCLOSURE OF THE INVENTION

The present invention provides a process for preparation of cyclopropylethanol, which comprises subjecting a 3-cyclopropyl-2,3-epoxypropionic acid ester (3-cyclopropyl-2-oxylanecarboxylic acid ester) to solvolysis in the presence of a base, treating the product of the solvolysis with an acid to obtain cyclopropylacetaldehyde, and reducing the obtained cyclopropylacetaldehyde.

The present invention also provides a process for preparation of cyclopropylethanol, which comprises reducing cyclopropylacetaldehyde.

The present invention further provides a process for preparation of cyclopropylacetaldehyde, which comprises subjecting a 3-cyclopropyl-2,3-epoxypropionic acid ester to solvolysis in the presence of a base, and treating the product of the solvolysis with an acid.

The present invention still further provides a process for preparation of cyclopropylacetonitrile, which comprises subjecting a 3-cyclopropyl-2,3-epoxypropionic acid ester to solvolysis in the presence of a base, treating the product of the solvolysis with an acid to obtain cyclopropylacetaldehyde, reacting the obtained cyclopropylacetaldehyde with hydroxylamine or salts thereof to obtain cyclopropylacetaldehyde oxime, and reacting the obtained cyclopropylacetaldehyde oxime with acetic anhydride.

The present invention still further provides a process for preparation of cyclopropylacetaldehyde oxime, which comprises subjecting a 3-cyclopropyl-2,3-epoxypropionic acid ester to solvolysis in the presence of a base, treating the product of the solvolysis with an acid to obtain cyclopropylacetaldehyde, and reacting the obtained cyclopropylacetaldehyde with hydroxylamine or salts thereof.

The present invention still further provides a process for preparation of cyclopropylacetaldehyde oxime, which comprises subjecting a 3-cyclopropyl-2,3-epoxypropionic acid ester to solvolysis in the presence of a base, and reacting the product of the solvolysis with a salt of hydroxylamine.

The present invention still further provides a process for preparation of cyclopropylacetonitrile, which comprises reacting cyclopropylacetaldehyde oxime with acetic anhydride.

The present invention still further provides cyclopropylacetaldehyde oxime.

MODES FOR CARRYING OUT THE INVENTION

The process (A) which comprises subjecting a 3-cyclopropyl-2,3-epoxypropionic acid ester to solvolysis in the presence of a base, treating the product of the solvolysis with an acid to obtain cyclopropylacetaldehyde, is explained.

Any ester of 3-cyclopropyl-2,3-epoxypropionic acid can, with no particular limitation, be used for this process as long as its ester group can undergo solvolysis. Examples of such ester are methyl ester, ethyl ester, propyl ester, isopropyl ester, n-butyl ester, isobutyl ester, pentyl ester and hexyl ester.

Examples of solvents usable for the process are water; alcohols, e.g. methanol, ethanol, propanol, isopropanol and butanol; and ethers, e.g. diisopropyl ether, tetrahydrofuran and dioxane. There are no specific restrictions with respect to the amount of the solvent used, but the amount is desirably in a range of 1 to 100 parts by weight based on the weight of the 3-cyclopropyl-2,3-epoxypropionic acid ester used, more preferably in a range of 1 to 10 parts by weight on the same basis.

Examples of the base are alkali metal hydroxides, e.g. sodium hydroxide, potassium hydroxide and lithium hydroxide; alkali metal carbonates, e.g. lithium carbonate, sodium carbonate and potassium carbonate; and alkali metal hydrogencarbonates, e.g. lithium hydrogencarbonate, sodium hydrogencarbonate and potassium hydrogencarbonate. The base is used desirably in an amount of 0.5 to 10 moles based on one mole of the 3-cyclopropyl-2,3-epoxypropionic acid ester used, more preferably in an amount of 1 to 1.5 moles on the same basis.

Addition of an acid to the mixture obtained by the solvolysis and containing the product yields cyclopropylacetaldehyde. Examples of the acid are inorganic acids, e.g. hydrochloric acid, sulfuric acid, nitric acid and phosphoric acid; organic acids, e.g. acetic acid, chloroacetic acid, propionic acid, butyric acid, formic acid, oxalic acid and malonic acid; and acidic ion-exchange resin. The acid is used desirably in an amount of 1 to 10 moles based on one mole of the 3-cyclopropyl-2,3-epoxypropionic acid ester used, more preferably in an amount of 1 to 1.5 moles on the same basis.

The solvolysis is carried out desirably at a temperature in a range of –20 to 150° C., more preferably in a range of 0 to 70° C. The reaction time for the solvolysis differs depending on the type and amount of the base or solvent used, but is generally in a range of 10 minutes to 24 hours. The acid treatment is carried out desirably at a temperature in a range of –20 to 100° C., more preferably in a range of 0 to 50° C. The time required for the acid treatment differs depending on the type and amount of the acid or solvent used, but is generally desirably in a range of 10 minutes to 24 hours.

The above reactions are carried out by, for example, mixing a 3-cyclopropyl-2,3-epoxypropionic acid ester with a base and a solvent, stirring the mixture at a prescribed temperature under reduced pressure or under atmospheric pressure and then adding an acid to the resulting mixture.

The reaction mixture thus obtained and containing cyclopropylacetaldehyde may as it is be supplied to the next reduction or reaction with hydroxylamine or salts thereof. Alternatively, the reaction mixture may be subjected to isolation and purification to give cyclopropylacetaldehyde, which is then supplied to the next reaction. In this case, the isolation and purification can be carried out by any process generally employed for isolation and purification of organic compounds. For example, the reaction mixture is poured into water, then the resulting mixture is extracted with an aliphatic hydrocarbon such as hexane, an aromatic hydrocarbon such as toluene, a halohydrocarbon such as dichloromethane or an ether such as diethyl ether or diisopropyl ether, and the obtained extract is, after condensation, purified by distillation, silica gel column chromatography or like methods.

The process (B) which comprises reducing cyclopropylacetaldehyde to obtain cyclopropylethanol is described next.

Any reduction process can be employed, as long as it can reduce aldehyde group. Examples of such process are, for example, (a) reduction with a metal hydride complex, (b) catalytic hydrogenation, and (c) reaction with a secondary alcohol in the presence of an aluminum alkoxide. These processes are described below.

(a) Reduction with a Metal Hydride Complex

Examples of metal hydride complexes usable for this purpose are sodium borohydride, sodium trimethoxyborohydride, sodium cyanoborohydride, lithium aluminum hydride, sodium triethoxyaluminum hydride, sodium bis(2-methoxyethoxy)aluminum hydride and diisobutylaluminum hydride. It is desirable to use one of these in an amount per mole of cyclopropylacetaldehyde of 0.1 to 10 moles, more preferably 0.25 to 2.0 moles.

The reaction is desirably carried out in the presence of a solvent. Any solvent can be used with no particular limitation for this purpose as long as it does not adversely affect the reaction. Examples of preferred solvents are ethers, e.g. diisopropyl ether, tetrahydrofuran and dioxane; and aromatic hydrocarbons, e.g. toluene, xylene and mesitylene. Where sodium borohydride, sodium trimethoxyborohydride or sodium cyanoborohydride is used as the metal hydride complex, water or an alcohol such as methanol, ethanol, propanol, isopropanol or butanol can also be used as the solvent besides the above ethers or aromatic hydrocarbons. The amount of the solvent used is, not particularly limited though, desirably in an amount of 1 to 100 parts by weight based on the weight of cyclopropylacetaldehyde, more preferably in an amount of 1 to 10 parts by weight on the same basis.

The reaction temperature is desirably in a range of –70 to 100° C., more preferably in a range of –20 to 50° C. The reaction time differs depending on the type and amount of the metal hydride complex or solvent used, but is generally in a range of 10 minutes to 24 hours.

The reaction is carried out by, for example, mixing cyclopropylacetaldehyde and a solvent, stirring the mixture at a prescribed temperature and then adding a metal hydride complex to the mixture; or by mixing a metal hydride complex and a solvent, stirring the mixture at a prescribed temperature and then adding cyclopropylacetaldehyde to the mixture.

(b) Catalytic Hydrogenation

This process is effected in the presence of a hydrogenation catalyst. Examples of the hydrogenation catalyst are Raney nickel, Raney cobalt, rhodium supported on activated charcoal, platinum oxide, platinum supported on activated charcoal, hexachloroplatinum and copper chromite. The hydrogenation catalyst is desirably used in an amount based on the weight of cyclopropylaldehyde of 0.01 to 20% by weight, more preferably 0.1 to 5% by weight.

The reaction is desirably carried out in the presence of a solvent. Any solvent can be used with no particular limitation for this purpose as long as it does not adversely affect the reaction. Examples of preferred solvents are water; alcohols, e.g. methanol, ethanol, propanol, isopropanol and butanol; ethers, e.g. diisopropyl ether, tetrahydrofuran and dioxane; and esters, e.g. methyl acetate and ethyl acetate. The amount of the solvent used is, not particularly limited though, desirably in an amount of 1 to 100 parts by weight based on the weight of cyclopropylacetaldehyde, more preferably in an amount of 1 to 10 parts by weight on the same basis.

The reaction temperature is desirably in a range of 0 to 100° C., more preferably in a range of 20 to 60° C. The reaction time differs depending on the type and amount of the hydrogenation catalyst or solvent used, but is generally in a range of 10 minutes to 24 hours.

The reaction is carried out by, for example, mixing cyclopropylacetaldehyde, a hydrogenation catalyst and a solvent, and subjecting the mixture to hydrogenation under atmospheric pressure or under pressure. The hydrogen pressure is desirably in a range of 1 to 50 kg/cm$^2$ (0.098 to 4.9 MPa)

(c) Reaction with a Secondary Alcohol in the Presence of an Aluminum Alkoxide

Examples of aluminum alkoxides usable for this process are aluminum trimethoxide, aluminum triethoxide, aluminum triisopropoxide, aluminum tri-n-butoxide and aluminum diisopropylate mono-sec-butylate, of which aluminum triisopropoxide is preferably used. The amount of the aluminum alkoxide used is desirably selected from a range of 0.1 to 10 mole % based on the mole of cyclopropylacetaldehyde, more preferably from a range of 1 to 10 mole % on the same basis.

Examples of secondary alcohols are isopropanol, 2-butanol, 2-pentanol, cyclobutanol, cyclopentanol and cyclohexanol, of which isopropanol is preferably used. The amount of the secondary alcohol used is desirably in a range of 1.0 to 100 moles per mole of cyclopropylacetaldehyde, more preferably 1.0 to 10 moles per mole thereof.

The reaction may be carried out either in the presence or absence of a solvent. Any solvent can be used with no particular limitation for this purpose as long as its does not adversely affect the reaction. Examples of usable solvents are aliphatic hydrocarbons, e.g. hexane, heptane and octane; aromatic hydrocarbons, e.g. benzene, toluene, xylene and mesitylene; and ethers, e.g. diisopropyl ether, tetrahydrofuran and dioxane. The amount of the solvent used is not particularly limited, but is desirably in a range of 1 to 100 parts by weight based on the weight of cyclopropylacetaldehyde, more preferably 1 to 10 parts by weight on the same basis.

The reaction temperature is desirably in a range of 0 to 150° C. The reaction time differs depending on the type and amount of the aluminum alkoxide, secondary alcohol or solvent used, but is generally in a range of 30 minutes to 20 hours.

The reaction is carried out by, for example, mixing cyclopropylacetaldehyde, an aluminum alkoxide, a secondary alcohol and, as necessary, a solvent, and stirring the mixture at a prescribed temperature and under atmospheric pressure or under reduced pressure. Where the ketone that is byproduced on the reaction has a boiling point lower than that of cyclopropylethanol, the reaction is desirably effected while the ketone is being distilled off.

The cyclopropylethanol thus obtained can be isolated and purified by any process generally employed for isolation and purification of organic compounds. For example, the reaction mixture is poured into water, then the resulting mixture is extracted with an aliphatic hydrocarbon such as hexane, an aromatic hydrocarbon such as toluene, a halohydrocarbon such as dichloromethane, or an ether such as diethyl ether or diisopropyl ether, and the obtained extract is, after condensation, purified by distillation, silica gel column chromatography or like methods.

Next, described is the process (c) which comprises reacting cyclopropylacetaldehyde with hydroxylamine or salts thereof to obtain cyclopropylacetaldehyde oxime.

Commercially available hydroxylamine salts are usable for this process. Examples of hydroxylamine salts are hydroxylamine sulfate, hydroxylamine hydrochloride and hydroxylamine phosphate. Free hydroxylamine can readily be prepared by treating a hydroxylamine salt with a base. Where a hydroxylamine salt is used, the reaction is therefore carried out in the presence of a base. Any base can be used for this purpose as long as it can convert hydroxylamine salts into free hydroxylamine. Examples of usable bases are alkali metal hydroxides, e.g. lithium hydroxide, sodium hydroxide and potassium hydroxide; and alkali metal carbonates, e.g. lithium carbonate, sodium carbonate and potassium carbonate, of which sodium hydroxide or sodium carbonate is preferably used. The amount of the base used is desirably in a range of 1 to 5 moles per mole of the hydroxylamine salt used, more preferably 1 to 1.5 moles per mole of the same. The amount of the hydroxylamine or salts thereof used is not specifically limited, but is desirably in a range of 0.5 to 2 moles per mole of cyclopropylacetaldehyde.

The reaction is desirably carried out in the presence of a solvent. Examples of usable solvents are water, and alcohols, e.g. methanol and ethanol, of which water is preferably used. The amount of the solvent used is not particularly limited, but is desirably such that the operability and capacity efficiency of the reaction are not impaired. The desirable amount is thus in a range of 1 to 10 parts by weight based on the weight of cyclopropylacetaldehyde.

The above reaction is carried out by, for example, adding cyclopropylacetaldehyde to a reaction vessel equipped with a stirrer and previously charged with hydroxylamine or salts thereof, a solvent and, as necessary, a base.

The reaction temperature is desirably in a range of about 0 to 100° C., more preferably in a range of 10 to 60° C. The reaction time differs depending on the reaction conditions employed, but is desirably in a range of 0.5 to 10 hours.

The cyclopropylacetaldehyde oxime thus obtained can be isolated and purified from the reaction mixture by any process generally employed for isolation and purification of organic compounds. For example, the reaction mixture is poured into water, then the resulting mixture is extracted with an aliphatic hydrocarbon such as hexane, an aromatic hydrocarbon such as toluene, a halohydrocarbon such as dichloromethane, or an ether such as diethyl ether or diisopropyl ether, and the obtained extract is, after condensation, purified by distillation, silica gel column chromatography or like methods. Alternatively, the extract can, as it is, be supplied to the next reaction with acetic anhydride.

Cyclopropylaldehyde oxime is, having been not given in the literature, a novel compound and is an important intermediate for synthesizing cyclopropylacetonitrile.

Next described is the process (D), which comprises subjecting a 3-cyclopropyl-2,3-epoxypropionic acid ester to solvolysis and reacting the solvolyzed product with a hydroxylamine salt to obtain cyclopropylacetaldehyde oxime.

The solvolysis of 3-cyclopropyl-2,3-epoxypropionic acid esters can be carried out in the same manner as for the solvolysis in the process (A).

The reaction of the product obtained by solvolysis with a hydroxylamine salt is carried out in the presence of a base. Any base can be used for this purpose as long as it can convert hydroxylamine salts into free hydroxylamine. Examples of usable bases are alkali metal hydroxides, e.g. lithium hydroxide, sodium hydroxide and potassium hydroxide; and alkali metal carbonates, e.g. lithium carbonate, sodium carbonate and potassium carbonate, of which sodium hydroxide or sodium carbonate is preferably used. The amount of the base used is desirably in a range of 1 to 5 moles per mole of the hydroxylamine salt used, more preferably 1 to 1.5 moles per mole of the same. The amount of the hydroxylamine salt used is not specifically limited, but is desirably in a range of 0.5 to 2 moles per mole of the 3-cyclopropyl-2,3-epoxypropionic acid ester used.

The reaction is desirably carried out in the presence of a solvent. Examples of usable solvents are water, and alcohols, e.g. methanol and ethanol, of which water is preferably used. The amount of the solvent used is not particularly limited, but is desirably such that the operability and capacity efficiency of the reaction are not impaired. The desirable amount is thus in a range of 1 to 10 parts by weight based on the weight of the 3-cyclopropyl-2,3-epoxypropionic acid ester used.

The reaction temperature is desirably in a range of about 0 to 100° C., more preferably in a range of 10 to 60° C. The reaction time differs depending on the reaction conditions employed, but is desirably in a range of 0.5 to 10 hours.

The above reaction is carried out by, for example, mixing a 3-cyclopropyl-2,3-epoxypropionic acid ester, a base and, as necessary, a solvent, stirring the mixture at a prescribed temperature and under reduced pressure or under atmospheric pressure, and then adding to the resulting mixture a hydroxylamine salt or an aqueous solution thereof.

The cyclopropylacetaldehyde oxime thus obtained can be isolated and purified from the reaction mixture by any process usually employed for isolation and purification of organic compounds. For example, the reaction mixture is poured into water, then the resulting mixture is extracted with an aliphatic hydrocarbon such as hexane, an aromatic hydrocarbon such as toluene, a halohydrocarbon such as dichloromethane, or an ether such as diethyl ether or diisopropyl ether, and the obtained extract is, after condensation, purified by distillation, silica gel column chromatography or like methods. Alternatively, the extract can, as it is, be supplied to the next reaction with acetic anhydride.

Next described is the process (E), which comprises reacting cyclopropylaldehyde oxime with acetic anhydride to obtain cyclopropylacetonitrile.

Acetic anhydride is desirably used in an amount of 1 to 20 moles per mole of cyclopropylacetaldehyde oxime, more preferably 1 to 5 moles per mole of the same.

The reaction can be carried out either in the presence or absence of a solvent. Examples of solvents desirably usable for this purpose are ethers, e.g. diisopropyl ether and dioxane; aromatic hydrocarbons, e.g. toluene, xylene and mesitylene; and esters, e.g. ethyl acetate and butyl acetate. The reaction is effected in solution or in slurry. The amount of the solvent used is not particularly limited, but is desirably in a range of 1 to 100 parts by weight based on the weight of cyclopropylacetaldehyde oxime, more preferably in a range of 1 to 10 parts by weight on the same basis.

The reaction temperature is desirably in a range of about 25 to 150° C., more preferably in a range of 50 to 100° C. The reaction time differs depending on the type and amount of the solvent used, but is desirably in a range of 10 minutes to 24 hours.

The reaction is carried out by, for example, mixing cyclopropylacetaldehyde oxime and a solvent, stirring the mixture at a prescribed temperature and then adding acetic anhydride to the resulting mixture.

The cyclopropylacetonitrile thus obtained can be isolated and purified from the reaction mixture by any process usually employed for isolation and purification of organic compounds. For example, the reaction mixture is poured into water, then the resulting mixture is extracted with an aliphatic hydrocarbon such as hexane, an aromatic hydrocarbon such as toluene, a halohydrocarbon such as dichloromethane, or an ether such as diethyl ether or diisopropyl ether, and the obtained extract is, after condensation, purified by distillation, silica gel column chromatography or like methods. Alternatively, the reaction mixture can as it is be purified by distillation.

The 3-cyclopropyl-2,3-epoxypropionic acid esters used in the present invention can be prepared by, for example, reacting cyclopropanecarbaldehyde with an α-haloacetic acid ester (see Japanese Patent Application Laid-open No. Hei 11-228559).

EXAMPLES

Hereinbelow, the present invention is described more concretely with reference to Examples, which are by no means limitative of the invention.

Reference Example 1

Synthesis of Methyl 3-cyclopropyl-2,3-epoxy-propionate

A 300-ml three-necked flask equipped with a thermometer and a stirrer was charged with 87 g (0.45 mole) of a 28% sodium methoxide solution in methanol and 21 g (0.30 mole) of cyclopropanecarbaldehyde and, after the contents had been cooled down to −10° C., 48.9 g (0.45 mole) of methyl chloroacetate was added dropwise over 3 hours. After completion of the addition, the reaction mixture was allowed to be warmed up to room temperature and was then stirred at room temperature for 5 hours. Thereafter, 12 g (0.20 mole) of acetic acid was added to neutralize remaining sodium methoxide and the resulting mixture was poured into 140 g of water. The reaction mixture thus obtained was extracted three times each with 50 ml of ethyl acetate and the extracts were washed with 50 ml of saturated salt water. The mixture thus washed was dried over anhydrous sodium sulfate and condensed. The residue was distilled under reduced pressure to yield, as distillates at 70 to 73° C. [6 mmHg (8.0 hPa)], 29.8 g (0.21 mole; yield: 70.0%) of methyl 3-cyclopropyl-2,3-epoxypropionate having the following properties.

$^1$H-NMR (270 MHz, CDCl$_3$, TMS, ppm) δ: 3.78 (3H, s), 3.30 (1H, d, J=2.0 Hz), 2.97 (1H, dd, J=2.0, 5.7 Hz), 1.00–0.80 (1H, m), 0.63–0.56 (1H, m), 0.46–0.41 (1H, m).

Example 1

Synthesis of Cyclopropylacetaldehyde

A 200-ml three-necked flask equipped with a cooler, a thermometer and a stirrer was charged with 48 ml (0.24 mole) of a 5N aqueous sodium hydroxide solution, to which 28.4 g (0.2 mole) of methyl 3-cyclopropyl-2,3-epoxypropionate obtained in the same manner as in Reference Example 1 was added dropwise at a temperature of 25° C. over 2 hours. After completion of the addition, the reaction mixture was stirred at 25° C. for 1 hour. Thereafter, 48 ml (0.24 mole) of 1.86N hydrochloric acid was added dropwise at 25° C. over 1 hour and then the mixture was stirred at 25° C. for 30 minutes. The reaction mixture thus obtained was extracted three times each with 50 ml of diethyl ether and the extracts were washed with 50 ml of saturated salt water. The mixture thus washed was dried over anhydrous sodium sulfate and condensed. The residue was purified by silica gel column chromatography, to yield 13.5 g (0.16 mole; yield: 80.5%) of cyclopropylacetaldehyde having the following properties.

$^1$H-NMR (270 MHz, CDCl$_3$, TMS, ppm) δ: 9.90–9.70 (1H, m), 2.33–2.25 (2H, m), 1.15–0.95 (1H, m), 0.65–0.58 (2H, m), 0.21–0.15 (2H, m).

Example 2

Synthesis of Cyclopropylethanol

A 100-ml three-necked flask equipped with a cooler, a thermometer and a stirrer was charged with 8.4 g (0.1 mole) of cyclopropylacetaldehyde obtained in the same manner as in Example 1 and 50 ml of diethyl ether. While the contents were being stirred at at a temperature of 25° C., 1.42 g (37.5 mmoles) of sodium borohydride was added over 15 minutes. After completion of the addition, the reaction mixture was stirred at 25° C. for 1 hour. Thereafter, the reaction mixture was neutralized with dilute hydrochloric acid. The reaction mixture thus obtained was extracted four times each with 30 ml of diisopropyl ether and the extracts were washed with 30 ml of saturated salt water. The mixture thus washed was dried over anhydrous sodium sulfate and condensed. The residue was purified by silica gel column chromatography, to yield 7.35 g (85.5 mmoles; yield: 85.5%) of cyclopropylethanol having the following properties.

$^1$H-NMR (270 MHz, CDCl$_3$, TMS, ppm) δ: 3.78–3.62 (2H, m), 1.75–1.56 (1H, m), 1.53–1.38 (2H, m), 0.80–0.60 (1H, m), 0.50–0.33 (2H, m), 0.13–0.03 (2H, m).

Example 3

Synthesis of Cyclopropylethanol

A 1-liter three-necked flask equipped with a cooler, a thermometer and a stirrer was charged with 144 ml (0.72 mole) of a 5N aqueous sodium hydroxide solution, to which 86.8 g (0.6 mole) of methyl 3-cyclopropyl-2,3-epoxypropionate obtained in the same manner as in Reference Example 1 was added dropwise at a temperature of 25° C. over 2 hours. After completion of the addition, the mixture was stirred at 25° C. for 1 hour. To the mixture 387 ml (0.72 mole) of 1.86N hydrochloric acid was added dropwise at 25° C. over 1 hour. After completion of the addition, the mixture was stirred at 25° C. for 30 minutes. Thereafter, the reaction mixture obtained was neutralized with saturated aqueous sodium hydrogencarbonate solution. To the obtained mixture 5.68 g (0.15 mole) of sodium borohydride was added over 30 minutes. After completion of the addition, the resulting mixture was stirred at 25° C. for 1 hour. The reaction mixture thus obtained was neutralized with dilute hydrochloric acid and then extracted four times each with 30 ml of diisopropyl ether, and the extracts were washed with 30 ml of saturated salt water. The mixture thus washed was dried over anhydrous sodium sulfate and condensed. The residue was purified by distillation [79° C., 60 mmHg (8.0 kPa)], to yield 32.5 g (0.38 mole; yield: 63.0%) of cyclopropylethanol.

Example 4

Synthesis of Cyclopropylacetaldehyde Oxime

A 50-ml three-necked flask equipped with a cooler, a thermometer and a stirrer was charged with 4.1 g (25.0 mmoles) of hydroxylamine sulfate and 50 g of water. The contents were neutralized with 2.0 g (50.0 mmoles) of sodium hydroxide. After stirring at room temperature for 30 minutes, 4.2 g (50.0 mmoles) of cyclopropylacetaldehyde obtained in the same manner as in Example 1 was added over 15 minutes. After completion of the addition, the reaction mixture was stirred at a temperature of 25° C. for 2 hours. The reaction mixture thus obtained was extracted three times each with 15 ml of isopropyl ether and the extracts were washed with 15 ml of saturated salt water. The mixture thus washed was dried over anhydrous sodium sulfate and condensed. The residue was purified by silica gel column chromatography, to yield 4.7 g (47.5 mmoles; yield: 95%) of cyclopropylacetaldehyde oxime having the following properties $^1$H-NMR (270 MHz, CDCl$_3$, TMS, ppm) δ: 7.80–6.90 (1H, m), 7.20–6.60 (1H, m), 2.20–1.75 (2H, m), 0.80–0.60 (1H, m), 0.50–0.33 (2H, m), 0.13–0.03 (2H, m).

Example 5

Synthesis of Cyclopropylacetaldehyde Oxime

A 200-ml three-necked flask equipped with a cooler, a thermometer and a stirrer was charged with 48 ml (0.24 mole) of a 5N aqueous sodium hydroxide solution, to which 28.4 g (0.2 mole) of methyl 3-cyclopropyl-2,3-epoxypropionate obtained in the same manner as in Reference Example 1 was added at a temperature of 25° C. over 2 hours. After completion of the addition, the reaction mixture was stirred at 25° C. for 1 hour. To the resulting mixture 18 g (0.11 mole) of hydroxylamine sulfate was added at 25° C. over 30 minutes and then the mixture was stirred at 25° C. for 2 hours. The reaction mixture thus obtained was extracted three times each with 50 ml of isopropyl ether and the extracts were washed with 50 ml of saturated salt water. The mixture thus washed was dried over anhydrous sodium sulfate and condensed. The residue was purified by silica gel column chromatography, to yield 13.9 g (0.14 mole; yield: 70.3%) of cyclopropylacetaldehyde oxime having the following properties.

$^1$H-NMR (270 MHz, CDCl$_3$, TMS, ppm) δ: 7.80–6.90 (1H, m), 7.20–6.60 (1H, m), 2.20–1.75 (2H, m), 0.80–0.60 (1H, m), 0.50–0.33 (2H, m), 0.13–0.03 (2H, m).

Example 6

Synthesis of Cyclopropylacetonitrile

A 50-ml three-necked flask equipped with a cooler, a thermometer and a stirrer was charged with 16.8 g (0.17 mole) of cyclopropylacetaldehyde oxime obtained in the same manner as in Example 4 and 20 ml of ethyl acetate as solvent. To the mixture 18.2 g (0.18 mole) of acetic anhydride was added at a temperature of 25° C. over 30 minutes. After completion of the addition, the reaction mixture was stirred for 3 hours under reflux. After the solvent had been distilled off, the residue was purified by distillation [75° C., 110 mmHg (14.7 kPa)], to yield 10.5 g (0.13 mole; yield: 76.7%) of cyclopropylacetonitrile having the following properties.

$^1$H-NMR (270 MHz, CDCl$_3$, TMS, ppm) δ: 2.41–2.33 (2H, d, J=6.92 Hz), 1.15–1.00 (1H, m), 0.79–0.70 (2H, m), 0.35–0.30 (2H, m).

INDUSTRIAL APPLICABILITY

According to the present invention, cyclopropylethanol and cyclopropylacetonitrile can be prepared at low costs and industrially advantageously.

The invention claimed is:

1. A process for preparation of cyclopropylethanol, which comprises subjecting a 3-cyclopropyl-2,3-epoxy-propionic acid ester to solvolysis in the presence of a base, treating the product of the solvolysis with an acid to obtain cyclopropylacetaldehyde, and reducing the obtained cyclopropylacetaldehyde.

2. A process for preparation of cyclopropylethanol, which comprises reducing cyclopropylacetaldehyde.

3. The process according to claim 1, wherein cyclopropylacetaldehyde is reduced with a metal hydride complex, or by catalytic hydrogenation, or by reaction with a secondary alcohol in the presence of an aluminum alkoxide, to yield cyclopropylethanol.

4. The process according to claim 1, wherein cyclopropylacetaldehyde is reduced with a metal hydride complex to yield cyclopropylethanol.

5. A process for producing cyclopropylacetaldehyde, which comprises subjecting a 3-cyclopropyl-2,3-epoxy-propionic acid ester to solvolysis in the presence of a base, and treating the product of the solvolysis with an acid.

6. A process for preparation of cyclopropylacetonitrile, which comprises subjecting a 3-cyclopropyl-2,3-epoxypropionic acid ester to solvolysis in the presence of a base, treating the product of the solvolysis with an acid to obtain cyclopropylacetaldehyde, reacting the obtained cyclopropylacetaldehyde with hydroxylamine or salts thereof to obtain cyclopropylacetaldehyde oxime, and reacting the obtained cyclopropylacetaldehyde oxime with acetic anhydride.

7. A process for preparation of cyclopropylacetaldehyde oxime, which comprises subjecting a 3-cyclopropyl-2,3-epoxypropionic acid ester to solvolysis in the presence of a base, treating the product of the solvolysis with an acid to obtain cyclopropylacetaldehyde, and reacting the obtained cyclopropylacetaldehyde with hydroxylamine or salts thereof.

8. A process for preparation of cyclopropylacetaldehyde oxime, which comprises subjecting a 3-cyclopropyl-2,3-epoxypropionic acid ester to solvolysis in the presence of a base, and treating the product of the solvolysis with a salt of hydroxylamine.

9. The process according to claim 6, wherein said salt of hydroxylamine is hydroxylamine sulfate or hydroxylamine chloride.

10. A process for preparation of cyclopropylacetonitrile, which comprises reacting cyclopropylacetaldehyde oxime with acetic anhydride.

11. Cyclopropylacetaldehyde oxime.

12. The process according to claim 2, wherein cyclopropylacetaldehyde is reduced with a metal hydride complex, or by catalytic hydrogenation, or by reaction with a secondary alcohol in the presence of an aluminum alkoxide, to yield cyclopropylethanol.

13. The process according to claim 2, wherein cyclopropylacetaldehyde is reduced with a metal hydride complex to yield cyclopropylethanol.

14. The process according to claim 7, wherein said salt of hydroxylamine is hydroxylamine sulfate or hydroxylamine chloride.

15. The process according to claim 8, wherein said salt of hydroxylamine is hydroxylamine sulfate or hydroxylamine chloride.

* * * * *